(12) United States Patent
Satoh et al.

(10) Patent No.: US 6,839,634 B1
(45) Date of Patent: Jan. 4, 2005

(54) METHOD FOR PREDICTING REACTION CHARACTERISTICS OF MOLECULES

(75) Inventors: Hiroko Satoh, Wako (JP); Kimito Funatsu, Toyohashi (JP); Tadashi Nakata, Wako (JP); Keiko Takano, Toshima-ku (JP)

(73) Assignee: The Institute of Physical and Chemical Research, Saitama-ken (JP)

( * ) Notice: Subject to any disclaimer, the term of this patent is extended or adjusted under 35 U.S.C. 154(b) by 0 days.

(21) Appl. No.: 09/266,813

(22) Filed: Mar. 12, 1999

(30) Foreign Application Priority Data

Sep. 11, 1998 (JP) ............................................. 10-258482

(51) Int. Cl.$^7$ ........................ G01Q 33/48; G01Q 33/50; G06F 101/00; G06G 7/48
(52) U.S. Cl. ............................ 702/19; 702/20; 702/22; 395/500.23; 703/11
(58) Field of Search ............................ 702/19, 20, 22; 395/500.23; 703/11

(56) References Cited

U.S. PATENT DOCUMENTS 5,025,388 A  6/1991  Cramer, III et al. ........ 364/496

OTHER PUBLICATIONS

Jain et al.; "Compass: Predicting Biological Activities from Molecular Surface Properties. Performance Comparisons on a Steriod Benchmark." Journal of Medicinal Chemistry, 1994, Bol. 37, No. 15, pp. 2315–2327.*
Lavender et al.; "Voronoi Diagrams of Set–Theoretic Solid Models." IEEE Computer Graphics & Applications, Sep. 1992, pp. 69–77.*
Chen et al.; "A 3D–QSAR Study on Ginkgolides and Their Analogues with Comparative Molecular Field Analysis." Bioorganic & Medicinal Chemistry Letters, 1998, vol. 8, pp. 1291–1296.*

Jain et al. Compass: predicting biological activities from molecular surface properties. Performance comparisons on a steroid benchmark. J. Med. Chem, vol. 37, pp. 2315–2327, 1994.*

Satoh et al. Classification of organic reactions: similarity of reactions based on changes in teh electronic features of oxygen atoms at the reaction sites. J. Chem. Inf. Comput. Sci., vol. 38, 210–219, 1998.*

Kim et al, J. Org. Chem. vol. 56, 1991, "Direction Prediction of Linear Free Energy Substituent Effects . . . ", pp. 2723–2729.

* cited by examiner

*Primary Examiner*—John Brusca
*Assistant Examiner*—Shubo (Joe) Zhou
(74) *Attorney, Agent, or Firm*—Jacobson Holman PLLC

(57) ABSTRACT

A molecule surrounding surface (20) is set so as to be reflected in the spatial dimension of a molecule. A molecule surrounding space surrounded by the molecule surrounding surface is divided into a plurality of component spaces (22), by which the reaction characteristic of the molecule is characterized. Probe points are provided on a frontier surrounding surface (5) on the molecule surrounding surface, and a space occupied rate is derived for each of the component spaces. Electrostatic energies are derived for each of the probe points on the frontier surrounding surface, and the sum of the electrostatic energies on the frontier surrounding surface is derived as a enelectrostatic factor of each of the component spaces. In addition, van der Waals energies are derived for each of the probe points, and the sum of the van der Waals energies on the frontier surrounding surface is derived as a steric factor of each of the component spaces. Assuming that the space occupied rate, the electrostatic factor and the steric factor are reaction characteristic values of the corresponding one of the component spaces, the reaction characteristic of the molecule is predicted on the basis of the reaction characteristic values of each of the component spaces.

18 Claims, 4 Drawing Sheets

▨ a : Hydrogen atom combined with Mg atom

▥ b : Hydrogen atom combined with B atom

▨ c : Carbon atom combined with Mg atom

▥ d : Carbon atom combined with B atom e: Reducing Agent f: Grignard Reagent g: Base

METHOD FOR PREDICTING REACTION CHARACTERISTICS OF MOLECULES

BACKGROUND OF THE INVENTION

1. Field of the Invention

The present invention relates generally to a method for predicting the reaction characteristics of molecules. More specifically, the invention relates to a molecular reaction characteristic predicting method for predicting a correlation characteristic between reaction characteristics of a plurality of molecules, and a reaction characteristic predicting map and computer-readable storage medium.

2. Related Background Art

In the development of a medicine, the prediction of activity and the design of the medicine are carried out. That is, a correlation between the structures of the ligand and an acceptor and/or the interaction therebetween and the pharmacological activity of the medicine on organisms is examined, and it is predicted whether the medicine to be designed has a desired activity, so that the medicine is designed.

In the field of synthetic chemistry, the prediction of reactivity and the design of synthesis are carried out. That is, a correlation between the structures of reactants and/or the interaction between the reactants and the reactivity thereof is examined, and it is predicted whether a sufficient amount of supposed reaction product can be obtained, so that the optimum synthetic route is designed.

In the field of development of medicines, the cooperative molecular field analysis (CoMFA) method is conventionally known as a method for predicting the activity characteristics of ligand molecules (see, e.g., R.D.III Cramer, et al., J. Am. Chem. Soc., 1988, 110, 5959).

In the CoMFA method, a CoMFA field is produced to give the three-dimensional expression of a chemical structure of ligand molecule. The CoMFA field is derived by forming, e.g., a rectangular parallelepiped-shaped region surrounding a molecule, the activity characteristic of which is to be predicted, considering lattice points, which are distributed in the surrounding region in the form of a lattice, as probe points, and putting probe atoms at the respective probe points to calculate energy of the interaction between the probe atoms and the components of the molecule, such as substituents.

In the CoMFA method, it is assumed that a portion occupying a major part of a molecule, the reaction characteristic of which is to be predicted, is a common skeleton serving as a common portion, and the substituted portions of molecules having a common skeleton are substituted by various substituents. On the basis of the correlation characteristics of the obtained CoMFA, the presence of similarity between the activity characteristics of the molecules having the common skeleton is determined.

However, in the CoMFA method, it is assumed that the molecules have the common skeleton, and when the prediction of the activity characteristic of a certain molecule is intended, the presence of similarity between activity characteristics is determined only between the certain molecule and another molecule having a common skeleton with the certain molecule.

Thus, it is not possible to determine the presence of similarity between reaction characteristics of molecules, which have quite different sizes and which do not have any common skeleton.

In addition, in the CoMFA method, a molecule, the reaction characteristic of which is to be predicted, is not decomposed into minute sites to derive characteristic values for each site, and one CoMFA field is obtained as the whole molecule. Therefore, it is not known how each of the sites of the molecule contributes to the reaction, so that it is not possible to accurately predict and consider the reaction characteristics of the molecule.

Moreover, in the CoMFA method, the rectangular parallelepiped surrounding the overlapped ligand molecules is different in accordance with the size of a target ligand molecule group, so that there is a limit that the obtained characteristic value depends on the target ligand molecule group.

In addition, the CoMFA method is applied to the prediction of activity and the design of a medicine in the development of the medicine, so that the CoMFA method can not be applied to the prediction of reactivity and the design of synthesis in the field of synthetic chemistry. There is no reaction characteristic predicting method serving as a guide to the prediction of reactivity and the design of synthesis in the field of synthetic chemistry and as a guide to the prediction of activity and the design of a medicine in the development of the medicine.

SUMMARY OF THE INVENTION

It is therefore an object of the present invention to eliminate the aforementioned problems and to provide a molecular reaction characteristic predicting method, which can be applied to a wide field of chemistry including the field of synthetic chemistry as well as the field of development of medicines and which can accurately predict the presence of similarity between reaction characteristics of various molecules without limitations on common skeleton, and a reaction characteristic predicting map and computer-readable storage medium.

In order to accomplish the aforementioned and other objects, according to one aspect of the present invention, there is provided a molecular reaction characteristic predicting method for predicting a reaction characteristic of a molecule, the method comprising the steps of: setting a molecule surrounding surface so as to be reflected in a spatial dimension of a molecule, and assuming that a space surrounded by the molecule surrounding surface is a molecule surrounding space; dividing the molecule surrounding space into a plurality of component spaces, by which a reaction characteristic of the molecule is characterized, in accordance with a predetermined space dividing procedure, and assuming that contour surfaces surrounding the component spaces are component surrounding surfaces; assuming that a portion of each of the component surrounding surfaces on the molecule surrounding surface is a frontier surrounding surface of each of the component spaces; providing probe points on the frontier surrounding surface of each of the component spaces at regular intervals; deriving a rate of the molecule surrounding space occupied by each of the component spaces, as a space occupied rate of each of the component spaces; deriving electrostatic energies between a unit charge set at each of the probe points and charges of all of atoms of the molecule, for each of the probe points on the frontier surrounding surface of each of the component spaces, and deriving the sum of the electrostatic energies on the frontier surrounding surface of a corresponding one of the component spaces, as an electrostatic factor of the corresponding one of the component spaces; deriving van der Waals energies between a probe atom, which is set at each of the probe points and which has a predetermined steric characteristic, and all of the atoms of the molecule, for each of the probe points on the frontier surrounding surface of each of the component spaces, and deriving the sum of the van der Waals energies on the frontier surrounding surface of the corresponding one of the component spaces, as a steric factor of the corresponding one of the component spaces; and assuming that the space occupied rate, the electrostatic factor and the steric factor are reaction characteristic values of the corresponding one of the component spaces, and predicting a reaction characteristic of the molecule on the basis of the reaction characteristic values of each of the component spaces.

The molecule surrounding surface may be an outermost contour enveloping surface formed by a plurality of atomic spherical surfaces, each of which extends around the center of each of the atoms of the molecule.

Each of the component spaces may be a space surrounding each of the atoms of the molecule.

Each of atomic spherical surfaces may be derived so as to extend around the center of each of the atoms of the molecule, and it may be assumed that a portion of each of the atomic spherical surfaces intersecting other atomic spherical surfaces is an interior spherical surface and that a portion of each of the atomic spherical surfaces other than the interior spherical surface is a frontier spherical surface, each of the component spaces being a space surrounded by a surface, which cuts the interior spherical surface, and the frontier spherical surface.

Each of atomic spherical surfaces may be derived so as to extend around the center of each of the atoms of the molecule, and it may be assumed that a portion of each of the atomic spherical surfaces intersecting other atomic spherical surfaces is an interior spherical surface and that a portion of each of the atomic spherical surfaces other than the interior spherical surface is a frontier spherical surface, the frontier surrounding surface being the frontier spherical surface.

Each of atomic spherical surfaces may be derived so as to extend around the center of each of the atoms of the molecule, and each of the atomic spherical surfaces may be a spherical surface having a van der Waals radius of each of the atoms or a radius which is obtained by commonly adding a predetermined thickness to the van der Waals radius of each of the atoms.

The molecule surrounding surface may be a surrounding surface which surrounds a space formed by the frontier molecule orbital of the molecule.

The predetermined space dividing procedure may comprise the Voronoi division of the molecule surrounding space using the center of each of the atoms of the molecule as a mother point, and each of the component spaces may be a Voronoi region formed by the Voronoi division.

The space occupied rate may be based on a volume of each of the component spaces.

The space occupied rate may be based on the number of the probe points existing on the frontier surrounding surface.

The space occupied rate may be based on an area of the frontier surrounding surface.

The electrostatic factor may be normalized by dividing the sum of the electrostatic energies on the frontier surrounding surface of a corresponding one of the component spaces by the space occupied rate of the corresponding one of the component spaces, and the steric factor may be normalized by dividing the sum of the van der Waals energies on the frontier surrounding surface of a corresponding one of the component spaces by the space occupied rate of the corresponding one of the component spaces.

The probe atom may be an $sp^3$ carbon, an $sp^2$ carbon or an sp carbon.

The molecular reaction characteristic predicting method may further comprise the steps of: deriving the space occupied rate, the electrostatic factor and the steric factor for each of the component spaces forming the molecule surrounding space of each of a plurality of molecules, the reaction characteristics of which are to be predicted; generating a plurality of sets of input data corresponding to the plurality of component spaces of each of the plurality of molecules, each set of the plurality of sets of input data being formed by the space occupied rate, the electrostatic factor and the steric factor; and processing the plurality of sets of generated input data in accordance with a technique of a self-organizing neural network to display the processed result on a reaction characteristic predicting map indicative of reaction characteristics of the plurality of molecules.

The molecular reaction characteristic predicting method may further comprise the step of: deriving the space occupied rate, the electrostatic factor and the steric factor for each of atoms of a plurality of molecules, the reaction characteristics of which are to be predicted; generating a plurality of sets of input data corresponding to the atoms of each of the plurality of molecules, each set of the plurality of sets of input data being formed by the space occupied rate, the electrostatic factor and the steric factor; and processing the plurality of sets of generated input data in accordance with a technique of a self-organizing neural network to display the processed result on a reaction characteristic predicting map indicative of reaction characteristics of the plurality of molecules.

The self-organizing neural network may be a Kohonen neural network, and the reaction characteristic predicting map may be a Kohonen map.

The Kohonen map may be displayed so as to be plane.

According to another aspect of the present invention, a molecular reaction characteristic predicting method comprising the steps of: describing atomic spherical surfaces, each of which surrounds a corresponding one of atoms of a molecule; assuming that a portion of each of the atomic spherical surfaces intersecting the atomic spherical surfaces of other atoms of the molecule is an interior spherical surface; assuming that a portion of each of the atomic spherical surfaces other than the interior spherical surface is a frontier spherical surface; providing probe points on each of the atomic spherical surfaces at regular intervals; deriving a rate of occupied space as a space occupied rate of a corresponding one of the atoms, for each of the atoms; deriving electrostatic energies between a unit charge set at each of the probe points and charges of all of the atoms of the molecule, for each of the probe points on the frontier spherical surface of each of the atoms; deriving the sum of the electrostatic energies on the frontier surrounding surface of a corresponding one of the atoms, as an electrostatic factor of the corresponding one of the atoms; deriving van der Waals energies between a probe atom, which is set at each of the probe points and which has a predetermined steric characteristic, and all of the atoms of the molecule, for each of the probe points on the frontier surrounding surface of each of the atoms; deriving the sum of the van der Waals energies on the frontier surrounding surface of the corresponding one of the atoms, as a steric factor of the corresponding one of the atoms; assuming that the space occupied rate, the electrostatic factor and the steric factor are reaction characteristic values of the corresponding one of the atoms; and predicting a reaction characteristic of the molecule on the basis of the reaction characteristic values of each of the atoms.

According to a further aspect of the present invention, there is provided a reaction characteristic predicting map for predicting a reaction characteristic of a molecule, wherein in accordance with the molecular reaction characteristic predicting method according to the one aspect of the present invention, the space occupied rate, the electrostatic factor and the steric factor are derived for each of the component spaces forming the molecular surrounding space of each of a plurality of molecules, the reaction characteristics of which are to be predicted, and a plurality of sets of input data are generated so as to correspond to the plurality of component spaces of each of the plurality of molecules, each set of the plurality of sets of input data being formed by the space occupied rate, the electrostatic factor and the steric factor, the plurality of sets of generated input data being processed in accordance with a technique of a self-organizing neural network, and the processed result being displayed so as to indicate reaction characteristics of the plurality of molecules.

According to a still further aspect of the present invention, there is provided a computer-readable storage medium having stored a program for predicting a reaction characteristic of a molecule, the program carrying out a process comprising the steps of: setting a molecule surrounding surface so as to be reflected in a spatial dimension of a molecule, and assuming that a space surrounded by the molecule surrounding surface is a molecule surrounding space; dividing the molecule surrounding space into a plurality of component spaces, by which a reaction characteristic of the molecule is characterized, in accordance with a predetermined space dividing procedure, and assuming that contour surfaces surrounding the component spaces are component surrounding surfaces; assuming that a portion of each of the component surrounding surfaces on the molecule surrounding surface is a frontier surrounding surface of each of the component spaces; providing probe points on the frontier surrounding surface of each of the component spaces at regular intervals; deriving a rate of the molecule surrounding space occupied by each of the component spaces, as a space occupied rate of each of the component spaces; deriving electrostatic energies between a unit charge set at each of the probe points and charges of all of atoms of the molecule, for each of the probe points on the frontier surrounding surface of each of the component spaces, and deriving the sum of the electrostatic energies on the frontier surrounding surface of a corresponding one of the component spaces, as an electrostatic factor of the corresponding one of the component spaces; deriving van der Waals energies between a probe atom; which is set at each of the probe points and which has a predetermined steric characteristic, and all of the atoms of the molecule, for each of the probe points on the frontier surrounding surface of each of the component spaces, and deriving the sum of the van der Waals energies on the frontier surrounding surface of the corresponding one of the component spaces, as a steric factor of the corresponding one of the component spaces; and assuming that the space occupied rate, the electrostatic factor and the steric factor are reaction characteristic values of the corresponding one of the component spaces, and predicting a reaction characteristic of the molecule on the basis of the reaction characteristic values of each of the component spaces.

Thus, the present invention can be applied to the wide field of chemistry including the field of synthetic chemistry as well as the field of development of medicines, and according to the present invention, it is possible to accurately predict the presence of similarity between reaction characteristics of various molecules, which have different sizes and so forth, without limitations on common skeleton.

DESCRIPTION OF THE PREFERRED EMBODIMENTS

Referring now to the accompanying drawings, the preferred embodiment of a molecular reaction characteristic predicting method according to the present invention will be described below. The molecular reaction characteristic predicting method of the present invention is a new technique for numerically characterizing the electronic and steric characteristics of a three-dimensional field surrounding a molecule, and named FRAU (Field-characterization for reaction analysis and understanding).

Figure 1:
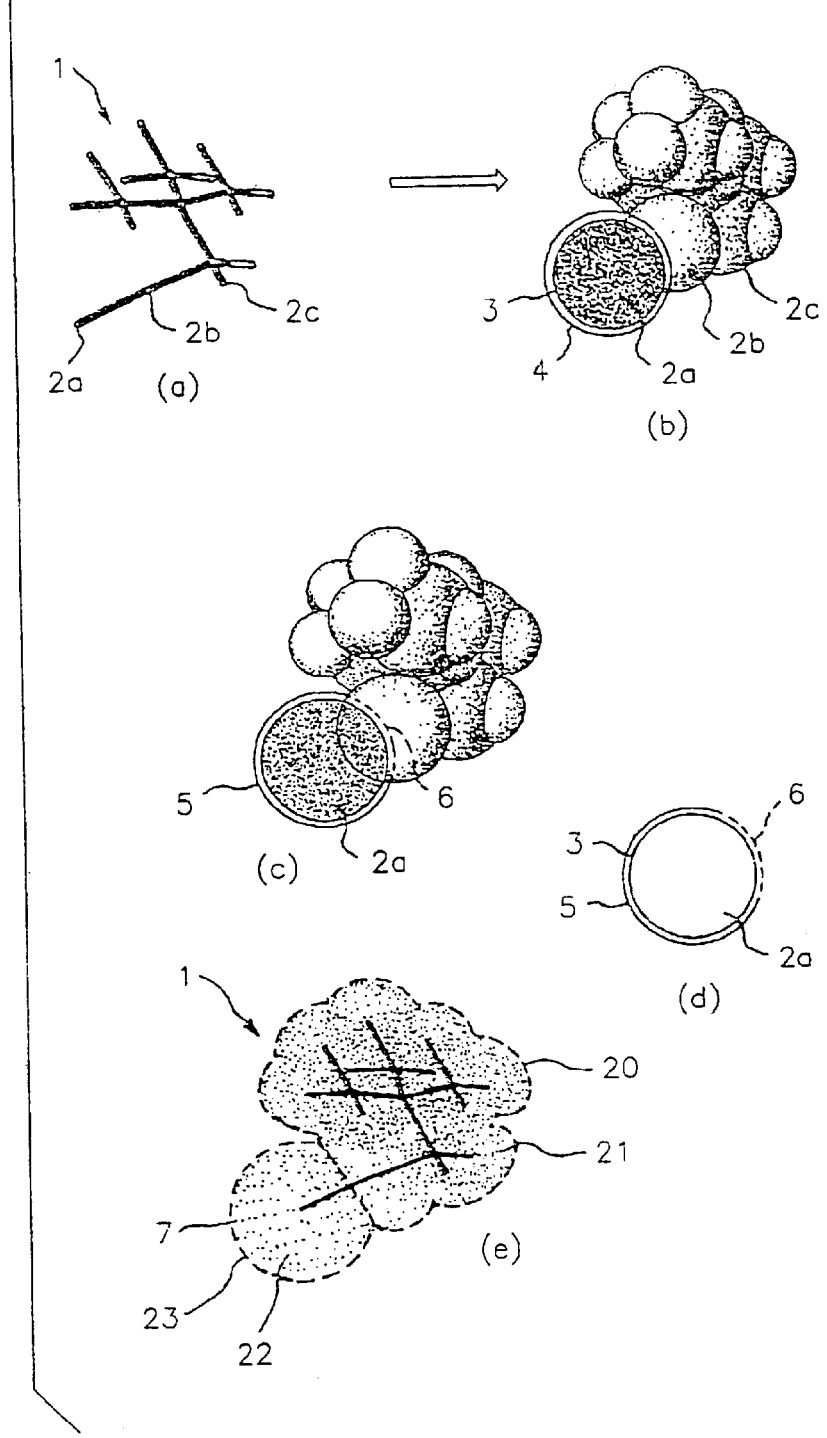
FIG. 1(a) is a schematic diagram showing a molecule, the reaction characteristic of which is to be predicted, as a tube model.
FIG. 1(b) is a schematic diagram showing the spherical surfaces of van der Waals radius of atoms of a molecule and atomic spherical surfaces.
FIG. 1(c) is a schematic diagram showing the interior spherical surface and frontier spherical surface of an atomic spherical surface.
FIG. 1(d) is a schematic diagram showing an atom extracted from the atoms of FIG. 1(c)
FIG. 1(e) is a schematic diagram showing probe points set on an atomic spherical surface at regular intervals, a molecule surrounding surface, a molecule surrounding space and component spaces.

First, in the FRAU, a molecule surrounding surface 20 (see FIG. 1(e)) is set so as to be reflected in the spatial dimension of a molecule. This molecule surrounding surface 20 may also be set as, e.g., a surrounding surface for surrounding a molecule surrounding space formed by a so-called frontier molecular orbital of the molecule. Alternatively, the molecule surrounding surface 20 may be set as an outermost contour enveloping surface formed by a plurality of atomic spherical surfaces 4, as will be described in detail later.

The molecule surrounding space 21 (see FIG. 1(e)) surrounded by the molecule surrounding surface 20 is divided into a plurality of component spaces 22 (see FIG. 1(e)) in accordance with a predetermined space dividing procedure. Each of the component spaces 22 is a space unit, by which the reaction characteristic of the molecule is characterized. It is assumed that the contour surfaces surrounding the component spaces 22 are component surrounding surfaces 23, and a portion of each of the component surrounding surfaces 23 on the molecule surrounding surface 20 is a frontier surrounding surface 5 (see FIG. 1(e)) of each of the component spaces 22.

When the molecule surrounding surface 20 is an outermost contour surrounding surface formed by the atomic spherical surfaces 4 of a plurality of atoms of a molecule, when a frontier spherical surface is adopted as the frontier surrounding surface 20 and when the number of probe points existing on the frontier spherical surface is adopted as a space occupied rate, the preferred embodiment of the present invention will be described below.

First, referring to FIGS. 1(a) through 1(e), a procedure for providing the characteristic value of a field surrounding a molecule will be described.

As shown in FIG. 1(a), a molecule 1, the reaction of which is to be predicted, schematically consists of a plurality of atoms 2a, 2b, 2c, . . . , which are bonded to each other by lattices.

In FIG. 1(b), reference number 3 denotes a spherical surface of van der Waals radius, which extends around the atomic center of an atom 2a and which has a van der Waals radius of, e.g., 1 through 2 angstroms. Similarly, spherical surfaces of van der Waals radius for other atoms of the molecule 1 are also shown.

In the FRAU of the present invention, the atomic spherical surface 4, which extends around the atomic center of the atom 2a and which has a radius greater than or equal to the van der Waals radius, is first described as shown in FIG. 1(b). The radius of the atomic spherical surface 4 is the van der Waals radius itself of each of the atoms, or a radius obtained by commonly adding a predetermined thickness, e.g., 1 angstroms, to the van der Waals radius of each of the atoms. The atomic spherical surface 4 is described for all of the atoms 2a, 2b, 2c, . . . of the molecule 1.

As shown in FIGS. 1(c) and 1(d), it is assumed that a portion of the atomic spherical surface 4 of each of the atoms intersecting the atomic spherical surfaces of other atoms is an interior spherical surface 6 and that a portion of the atomic spherical surface 4 other than the interior spherical surface 6 is a frontier spherical surface 5. FIG. 1(d) shows the frontier spherical surface 5 and interior spherical surface 6 of the atom 2a, which is extracted from the molecule 1. The frontier spherical surface 5 is a portion exposed to the outside, so that it can be supposed that the frontier spherical surface 5 be a region mainly concerning in a chemical reaction.

Each of the component spaces corresponds to a space surrounded by a surface, which cuts the interior spherical surface 6, and the frontier spherical surface 5.

Then, as shown in FIG. 1(e), probe points 7 are set on the atomic spherical surface 4 at regular intervals. Each of the probe points 7 is a point for diagnosing the characteristics of the molecule 1 at that position.

In the FRAU, in order to numerically characterize the electronic and steric factors of the molecule 1, three kinds of features are estimated. The three kinds of features include a space occupied rate (FF field), an electrostatic feature (FF electro) and a steric feature (FF steric). These features are called FRAU features (FF). The FRAU characteristics (FF) are operated for each of the atoms 2a, 2b, 2c, . . . of the molecule 1.

The space occupied rate (FF field) is given as the number of the probe points 7 existing on the frontier spherical surface 5 of each of the atoms 2a, 2b, 2c, . . . . The fact that the space occupied rate (FF field) is large shows that the proportion occupied by the characteristic of the corresponding atom in the whole reaction characteristic of the molecule 1 is large.

The electrostatic energies between a unit charge set at each of the probe points 7 and charges of all of the atoms 2a, 2b, 2c, . . . of the molecule 1 are derived for each of the probe points 7 on the frontier spherical surface 5 of each of the atoms, and summed up for the probe points 7 on the frontier spherical surface 5 of the corresponding atom to give the electrostatic feature (FF electro), which is calculated by equation (1).

$$FFelectro = \left\{ \sum_{i=1}^{FFfield} \sum_{j=1}^{natom} 331.8417 \times charge(j)/r_{ij} \right\} \Big/ FFfield \text{ (kcal/mol)} \quad (1)$$

In the equation (1), natom denotes the number of atoms of the molecule 1, charge (j) denoting the charge of each of the atoms, and FF field denoting the space occupied rate. The fact that the electrostatic factor (FF electro) is large shows that a molecule, which has a positive charge and which is to be reacted with the molecule 1, is difficult to approach to (or 'attack to') the molecule 1.

The van der Waals energies between probe atoms having a predetermined steric characteristic set at the probe points 7 and all of the atoms of the molecule are derived for each of the probe points 7 on the frontier spherical surface 5 of each of the atoms, and the steric factor (FF steric) is given as the sum of the van der Waals energies on the frontier spherical surface 4 of the corresponding atom. The steric feature (FF steric) is estimated using a mathematical technique for calculating a van der Waals energy in a molecular force field MM3, and the steric feature (FF steric) is calculated by equation (2)

$$FFsteric = \left[ \sum_{i=1}^{FFfield} \sum_{j=1}^{natom} \sqrt{\varepsilon_i \times \varepsilon_j} \left\{ 1.84 \times 10^5 \exp\left(-12.0 \Big/ \frac{r_i + r_j}{r_{ij}}\right) - 2.25 \times \left(\frac{r_i + r_j}{r_{ij}}\right)^6 \right\} \right] \Big/ FFfield \text{ (kcal/mol)} \quad (2)$$

For example, sp³ carbon, sp² carbon or sp carbon is preferably used as the probe atom. In the equation (2), sp³ carbon is used as the probe atom. In the equation (2), ε denotes a parameter of MM3 indicative of the hardness of an atom, $r_i$ (or $r_j$) denoting a van der Waals radius defined in the MM3, $r_{ij}$ denoting a distance between a number i probe point and a number j atom on the frontier spherical surface 5 of the corresponding atom. The fact that the steric feature (FF steric) is large shows that a molecule to be reacted with the molecule 1 is difficult to approach to (or 'attack to') the molecule 1 since the steric hinderance is large.

Furthermore, in the above description, while the number of probe points 7 existing on the frontier spherical surface 5 of each of the atoms 2a, 2b, 2c, . . . has been adopted as the space occupied rate (FF field), the area of the frontier spherical surface 5 of each of the atoms 2a, 2b, 2c, may be adopted as the space occupied rate (FF field). The adoption of the area of the frontier spherical surface 5 as the space occupied rate (FF field) is useful for the case where the area of the frontier spherical surface 5 is analytically derived.

In the above description, it has been assumed that the molecule surrounding surface 20 be first set so as to be reflected in the spatial dimension of the molecule, and the outermost contour enveloping surface formed by the plurality of atomic spherical surfaces 4 has been adopted as the molecule surrounding surface. However, it may be considered that the atomic spherical surface 4 is derived for each of the plurality of atoms 2a, 2b, 2c, . . . of the molecule 1 using the center of each of the atoms as the center of the spherical surface without the premise that the molecule surrounding surface is first set, so that the molecule surrounding surface is obtained as the outermost contour enveloping surface formed by the plurality of atomic spherical surfaces 4.

In the above description, while the plurality of atomic spherical surfaces 4 have been derived to divide the molecule surrounding space 21 into the plurality of component spaces 23, the procedure for spatially dividing the molecule surrounding space 21 into the plurality of component spaces should not be limited thereto.

For example, the molecule surrounding surface 20 may be Voronoi-divided into a plurality of component spaces. In this case, Voronoi regions obtained by the Voronoi division are used as component spaces 22. For that purpose, a molecule surrounding surface 20 is first set by the frontier molecular orbital of a molecule. Then, in accordance with a technique of Voronoi diagram (e.g., see ACMC onputting Surveys, vol.23, no.3 (1991), pp.345–405 (translated into Japanese by Kokichi Sugihara, Voronoi Diagram-Introduction to One Basic Geometrical Data Structure, bit 1993, Separate Volume of the September Number, Computer Science, Kyoritu Shuppan, Tokyo, 1993, pp.131–185)), the centers of the atoms 2a, 2b, 2c, . . . of the molecule 1 are used as mother points to Voronoi-divide the molecule surrounding space 21 surrounded by the molecule surrounding surface 20 to obtain a Voronoi region for each atom. The contour surface of the obtained Voronoi region comprises a frontier surrounding surface on the molecule surrounding surface 20, and a boundary surface to the adjacent Voronoi region.

When the Voronoi region is adopted as the component space 22, the Voronoi region is preferably corrected by weighting on the basis of the ratio of the van der Waals radius of each of atoms and Voronoi-dividing in order to reflect the difference in size of the atoms 2a, 2b, 2c, of the molecule 1.

When the Voronoi region is adopted as the component space 22, the quantity for the volume of the Voronoi region is preferably adopted as the space occupied rate (FF field).

If the Voronoi region is adopted as the component space 22 as described above, the following advantages can be obtained. That is, it is possible to select a molecule surrounding space suitable for the object of applying a molecular reaction characteristic predicting method according to the present invention. For example, it is also possible to set a component space for each functional group while reflecting the characteristic of the functional group.

Figure 2:
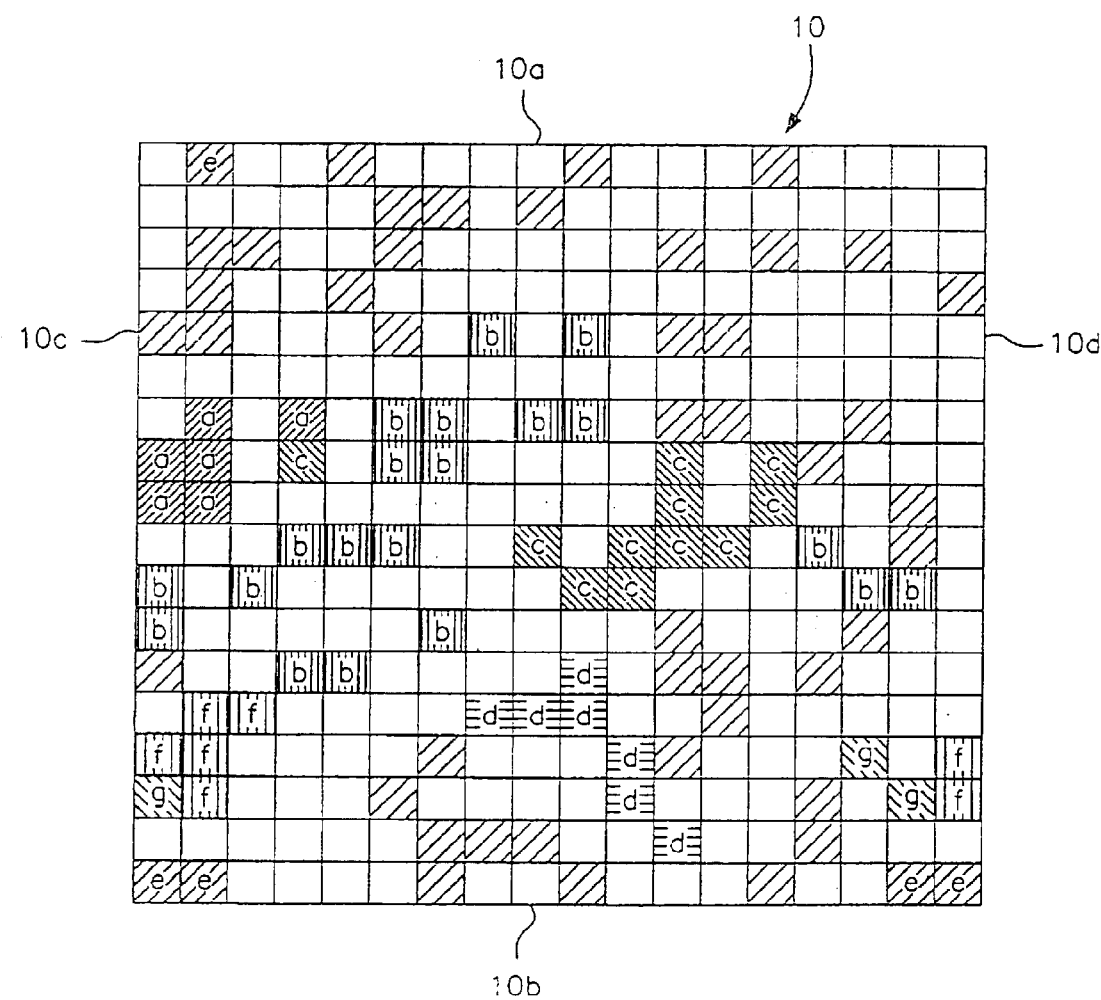
FIG. 2 is a view showing a Kohonen map obtained by the present invention, wherein each of small unit rectangles shows a neuron.
Figure 3:
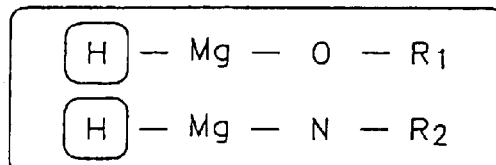
FIG. 3 is a schematic diagram showing a molecule specified by indicative signs shown in the Kohonen map of FIG. 2.
Figure 3:
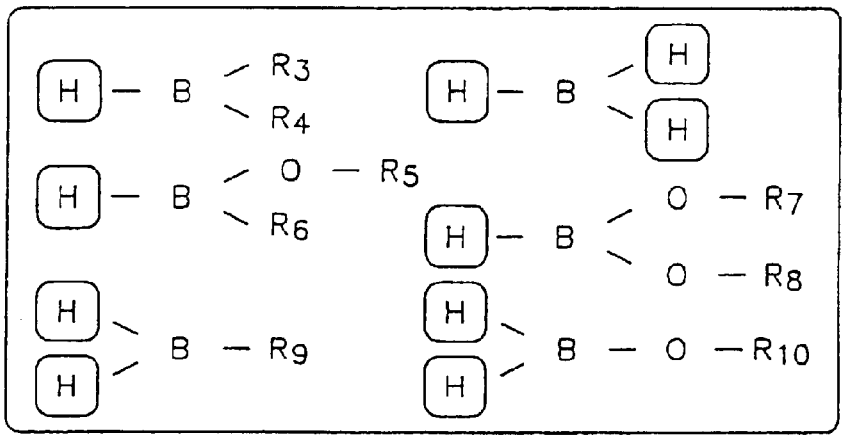
Figure 3:
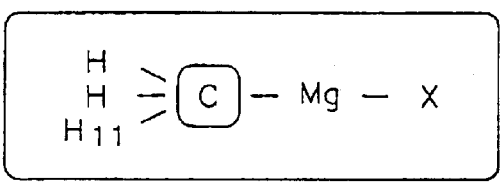
Figure 3:
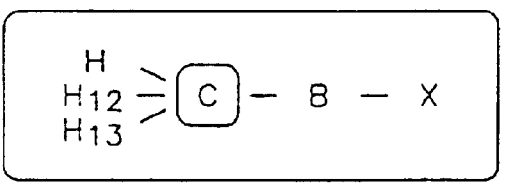
Figure 4:
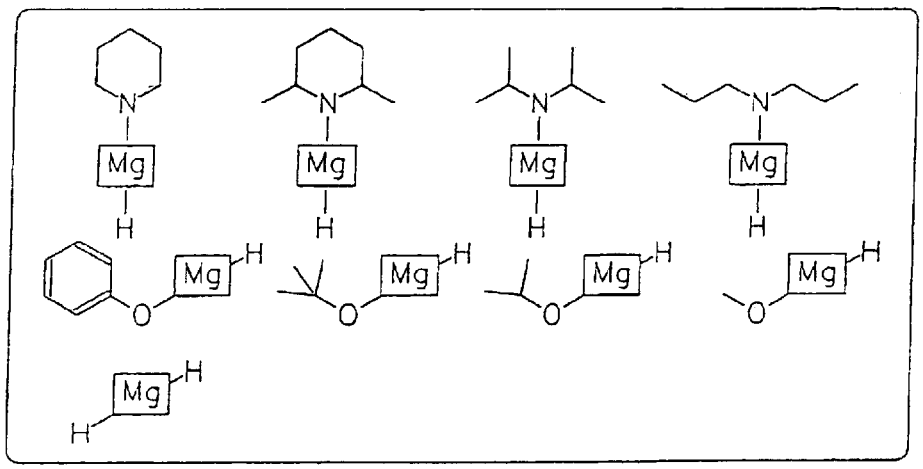
FIG. 4 is a schematic diagram showing a molecule specified by indicative signs shown in the Kohonen map, similar to FIG. 3.
Figure 4:
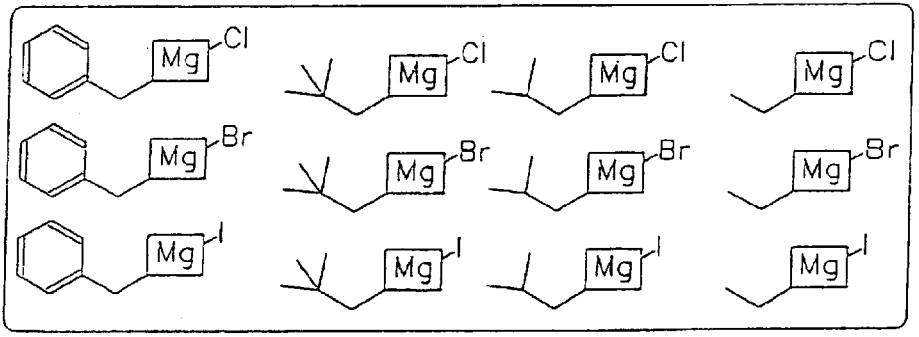
Figure 4:
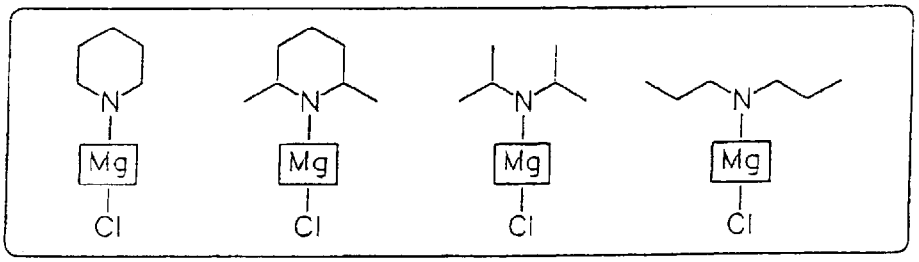

Referring to FIGS. 2 through 4, an applied example of the FRAU will be described below.

The effectiveness of the FRAU feature (FF) as an indication data indicative of the similarity and difference between molecular reaction characteristics will be demonstrated as follows.

As shown in FIGS. 3 and 4, 42 kinds of metallic reagents mainly containing Mg or B atom will be described as examples. Each of the metallic reagents is suitable for the verification of effectiveness of the FRAU since it has some functions.

In FIGS. 3 and 4, metallic reagents having similar characteristics are classified by unit rectangles expressed by signs "a", "b", . . . , "e", "f", and "g".

In the metallic reagents shown in FIGS. 3 and 4, the FRAU features (FF) of each of 152 atoms in total is obtained for Mg, B, hydrogen, carbon atoms and so forth.

For that purpose, the geometries and electronic structures of the aforementioned metallic reagents were first optimized by ab initio RHF/3-21G**(molecularorbital (MO)) calculations. Then, the FRAU features (FF) of each of the atoms of the metallic reagents was estimated using the aforementioned optimized geometries structure and the atomic charges. The atomic spherical surface 4 having a radius equal to the van der Waals radius was adopted to put a unit charge of +1 at the probe point 7 to derive an electrostatic feature (FF electro). An $sp^3$ carbon was used as a probe carbon to derive a steric feature (FF steric). For magnesium (Mg) atom, hydrogen atom and carbon atom of the metallic reagents shown in FIGS. 3 and 4, the FRAU features (FF) of 152 atoms in total were derived as the FRAU features (FF) of each of the atoms of the metallic reagents.

Moreover, the FRAU feature (FF) was used as an identification data to analyze the aforementioned set of metallic reagents using the technique of Kohonen neural network (see T. Kohonen, Biol. Cybern. 1982, 43, 59.), which is one of self-organizing neural networks.

The Kohonen neural network projects input data in a multidimensional space onto a Kohonen map while preserving a topology relationship between the input data. The boundary between groups, into which data in the Kohonen map have been classified, is recognized by, e.g., the U-matrix (see A. Ultsch, et al., Proc. Transputer Anvender Treffen/World Transputer Congress TAT/WTC 93 Aachen, Springer-verlag, New York, 1993, pp.194–203).

FIG. 2 shows a Kohonen map 10 obtained as a reaction characteristic predicting map. In the Kohonen map 10, each of small unit rectangles denotes a neuron. The Kohonen map 10 includes 18×18 neurons so as to include 152 target atoms, such as Mg, B, hydrogen and carbon atoms, in the metallic reagents shown in FIGS. 3 and 4.

A three-dimensional vector corresponding to the values of a space occupied rate (FF field), an electrostatic feature (FF electro) and a steric feature (FF steric), which are three kinds of FRAU features (FF), is formed by these FRAU features (FF). One three-dimensional vector formed by the three kinds of FRAU features (FF) is an input data to the Kohonen map 10. Herein, 152 input data exist.

A process for preparing the Kohonen map 10 will be described below.

The 152 input data are fired in the respective neurons of the Kohonen map 10 as follows.

First, in the initial state, three-dimensional vectors having various magnitude and directions in each of neurons are previously distributed in the Kohonen map 10 at random. Then, the Kohonen map 10 in the initial state is trained by the three-dimensional vector of the input data so as to be reflected in the three-dimensional vector distribution of the input data. This training is achieved by repeating an operation for modifying a vector between a neuron having the Euclidean distance nearest the three-dimensional vector of the input data and a neuron adjacent thereto by a predetermined technique so as to have the same magnitude and direction as those of the three-dimensional vector of the input data, for all of the input data predetermined times. Finally, the vectors of the neurons on the Kohonen map thus trained, and the input data having the nearest Euclidean distance are allocated to the neurons. Thus, all of the input data (152 input data) are allocated to obtain the Kohonen map 10 shown in FIG. 2.

The Kohonen map 10 shown in FIG. 2 actually has a torus shape. The uppermost line 10a and the lowermost line 10b show the same line, and the left line 10c and the right line 10d show the same line.

In the Kohonen map 10 shown in FIG. 2, the unit rectangles represented by the signs "a", "b", ..., "e", "f" and "g" correspond to the metallic reagents represented by the same classifying signs shown in FIGS. 3 and 4.

For simple explanation, a part of 152 input data will be described below.

In the Kohonen map 10, groups are formed and distributed in accordance with the kind of atoms.

In the Kohonen map 10, the distribution of magnesium (Mg) atoms, hydrogen atoms and carbon atoms of the metallic reagents shown in FIGS. 3 and 4 is shown.

When the distribution of hydrogen (H) atoms in FIG. 2 is viewed in detail, it can be seen that groups are formed on the basis of the difference in bonded metallic atoms. That is, hydrogen atoms ("a" in FIG. 3) bonded to magnesium (Mg) atoms and hydrogen atoms ("b" in FIG. 3) bonded to boron (B) atoms form groups, respectively.

When the distribution of carbon (C) atoms is viewed in detail, it can be seen that groups are formed on the basis of the difference in bonded metallic atoms. That is, carbon atoms ("c" in FIG. 3) bonded to magnesium (Mg) atoms and carbon atoms ("d" in FIG. 3) bonded to boron (B) form groups, respectively.

When the distribution of magnesium (Mg) atoms is viewed in detail, it can be seen that groups are formed every role in a reaction (as described above, the upper and lower lines and the right and left lines are connected to each other, respectively, since the actual shape of the Kohonen map 10 is a torus shape). That is, groups are formed by reducing agents ("e" in FIG. 3), Grignard reagents ("f" in FIG. 3) and bases ("g" in FIG. 3), respectively. Moreover, the distance between the Grignard reagent group and the base group was less than the distance between the Grignard reagent group and the reducing agent group and the distance between the base group and the reducing agent group. The boundary obtained by the U-matrix method was low (i.e., the difference was small) between the Grignard reagent group and the base group, and high (i.e., the difference was great) between the Grignard reagent group and the reducing agent group and between the base group and the reducing agent group.

These results are not substantially contradictory to the fact that the Grignard reagent is a strong base in a different view and belongs to the same base although it has a different strength, and the fact that the Grignard reagent is a magnesium salt of an alkane in another view and the base shown herein is a similar compound which is a magnesium salt of an amine. This shows that the FRAU characteristic values reflect the natural characteristics of a compound.

Moreover, when the respective contents of the Grignard reagent group, the base group and the reducing agent group are examined in detail, it can be seen that the groups are positioned near other groups of similar structures although this is not shown herein. For example, the Grignard reagents are positioned near those having common alkyl chains.

As described above, by the analysis using the Kohonen neural network, it was possible to clarify that the FRAU features are reflected in the similarities between structures and between roles in a reaction.

Moreover, it was possible to know which FRAU feature mainly determines the boundary line between groups, by fully examining the contents of the respective values of FRAU features on the respective neurons and the difference in each of the values of FRAU features between adjacent neurons, although this is not shown herein. That is, it was possible to know which FRAU feature is greatly related to the similarity between structures of reagents and the similarity between roles in the reaction.

Thus, if the technique combining the FRAU features with the analysis using the Kohonen neural network is used, there is a possibility that the contents of reaction characteristics of a compound can be clarified.

As described above, it is recognized by the Kohonen map 10 that the atoms having the same kind of reaction characteristic gather at the same or adjacent neuron.

It can be seen from FIGS. 2 through 4 that there is a very good correlation between the FRAU feature (FF) obtained according to the FRAU and the role and structure of the metallic reagent.

As described above, the FRAU can numerically characterize the electronic and steric features around the molecule 1 as the FRAU features. Moreover, the FRAU can apply the FRAU features to each of sites obtained by minutely dividing the molecule 1, i.e., each of atoms of the molecule 1.

In addition, the FRAU can apply the Kohonen neural network to show which element or site mainly controls the reaction and what degree the element or site contributes to the reaction. Thus, it is possible to quantitatively analyze and understand the reaction characteristics of the molecule.

Moreover, if a program corresponding to the aforementioned technique using the FRAU is stored in a computer-readable storage medium, the FRAU feature (FF) can be very quickly operated by means of a computer using the storage medium.

Furthermore, while the Kohonen neural network has been applied as a self-organizing neural network, other self-organizing neural networks can be applied.

What is claimed is:

1. A molecular reaction characteristic predicting method for predicting a reaction characteristic of a molecule, said method comprising the steps of:

setting a molecule surrounding surface surrounding the molecule so as to be reflected in a spatial dimension of the molecule, and assuming that a space surrounded by said molecule surrounding surface is a molecule surrounding space;

dividing said molecule surrounding space into a plurality of component spaces, by which a reaction characteristic of said molecule is characterized, in accordance with a predetermined space dividing procedure, and assuming that contour surfaces surrounding said component spaces are component surrounding surfaces, said molecule surrounding space being divided so that each component space of the plurality of component spaces includes therein each one atom composing the molecule;

assuming that a portion of each of said component surrounding surfaces appearing outside on said molecule surrounding surface is a frontier surrounding surface of each of said component spaces;

providing probe points on said frontier surrounding surface of each of said component spaces at regular intervals, deriving a rate of said molecule surrounding space occupied by each of said component spaces, as a space occupied rate of each of said component spaces;

deriving electrostatic energies between a unit charge set at each of said probe points and charges of all of atoms of said molecule for each of said probe points on said frontier surrounding surface of each of said component spaces, and deriving the sum of said electrostatic energies on said frontier surrounding surface of a corresponding one of said component spaces, as an electrostatic factor of said corresponding one of said component spaces;

deriving van der Waals energies between a probe atom, which is set at each of said probe points and which has a predetermined steric characteristic, and all of said atoms of said molecule, for each of said probe points on said frontier surrounding surface of each of said component spaces, and deriving the sum of said van der Waals energies on said frontier surrounding surface of said corresponding one of said component spaces, as a steric factor of said corresponding one of said component spaces;

assuming that said space occupied rate, said electrostatic factor and said steric factor are reaction characteristic values of said corresponding one of said component spaces, deriving the reaction characteristic values for all the component spaces of a predicting molecule of which a reaction characteristic is to be predicted, forming a predicting vector having a plurality of vector components selected from the reaction characteristic values of the predicting molecule, selecting a plurality of data molecules, a reaction characteristic of each of the data molecules being known, deriving, the reaction characteristic values for all the component spaces of each of the data molecules, forming a data vector for each of the data molecules, the data vector being corresponding to the predicting vector and having a plurality of vector components selected from the reaction characteristic values of each of the data molecules, estimating a Euclid distance between the predicting vector and each data vector and getting a plurality of Euclid distances between the predicting vector and all the data molecules, and predicting the reaction characteristic of the predicting molecule to be that the reaction characteristic of the predicting molecule is more similar to a reaction characteristic of a data molecule related to a shorter Euclid distance.

2. A molecular reaction characteristic predicting method as set forth in claim 1, wherein said molecule surrounding surface is an outermost contour enveloping surface formed by a plurality of atomic spherical surfaces, each of which extends around the center of each of said atoms of said molecule.

3. A molecular reaction characteristic predicting method as set forth in claim 1, wherein each of atomic spherical surfaces is derived so as to extend around the center of each of said atoms of said molecule, and wherein each of said atomic spherical surfaces is a spherical surface having a van der Waals radius of each of said atoms or a radius which is obtained by commonly adding a predetermined thickness to said van der Waals radius of each of said atoms.

4. A molecular reaction characteristic predicting method as set forth claim 1, wherein said molecule surrounding surface is a surrounding surface which surrounds a space formed by the frontier molecular orbital of said molecule.

5. A molecular reaction characteristic predicting method as set forth in claim 1, wherein said predetermined space dividing procedure comprises the Voronoi division of said molecule surrounding space using the center of each of said atoms of said molecule as a mother point, and each of said component spaces is a Voronoi region formed by said Voronoi division.

6. A molecular reaction characteristic predicting method as set forth in claim 1, wherein said space occupied rate is based on a volume of each of said component spaces.

7. A molecular reaction characteristic predicting method as set forth in claim 1, wherein said space occupied rate is based on the number of said probe points existing on said frontier surrounding surface.

8. A molecular reaction characteristic predicting method as set forth in claim 1, wherein said space occupied rate is based on an area of said frontier surrounding surface.

9. A molecular reaction characteristic predicting method as set forth in claim 1, wherein said electrostatic factor is normalized by dividing said sum of said electrostatic energies on said frontier surrounding surface of a corresponding one of said component spaces by said space occupied rate of said corresponding one of said component spaces, and said steric factor is normalized by dividing said sum of said van der Waals energies on said frontier surrounding surface of a corresponding one of said component spaces by said space occupied rate of said corresponding one of said component spaces.

10. A molecular reaction characteristic predicting method as set forth in claim 1, wherein said probe atom is an $sp^3$ carbon, an $sp^2$ carbon or an sp carbon.

11. A molecular reaction characteristic predicting method as set forth in claim 1, which further comprises the steps of:

processing the plurality of data vectors for the data molecules in accordance, with a technique of a self-organizing neural network to display the processed result on a reaction characteristic predicting map indicative of reaction characteristics of said plurality of molecules, and predicting the reaction characteristic of the predicting molecule based on the map.

12. A molecular reaction characteristic predicting method as set forth in claim 11, wherein said self-organizing neural network is a Kohonen neural network, and said reaction characteristic predicting map is a Kohonen map.

13. A molecular reaction characteristic predicting method as set forth in claim 12, wherein said Kohonen map is displayed so as to be plane.

14. A molecular reaction characteristic predicting method for predicting a reaction characteristic of a molecule said method comprising the steps of:

setting a molecule surrounding surface surrounding the molecule so as to be reflected in a spatial dimension the molecule, and assuming that a space surrounded by said molecule surrounding surface is a molecule surrounding space;

dividing said molecule surrounding space into a plurality of component spaces by which reaction characteristic of said molecule is characterized in accordance with a predetermined space dividing procedure and assuming that contour surfaces surrounding said component spaces are component surrounding surfaces said molecule surrounding space being divided so as that each component space of the plurality of component spaces includes therein each one atom composing the molecule;

assuming that a portion of each of said component surrounding surfaces appearing outside on slid molecule surrounding surface is a frontier surrounding surface of each of said component spaces;

wherein each of atomic spherical surfaces is derived so as to extend around the center of each of said atoms of said molecule, and wherein it is assumed that a portion of each of said atomic spherical surfaces intersecting other atomic spherical surfaces is an interior spherical surface and that a portion of each of said atomic spherical surfaces other than said interior spherical surface is a frontier spherical surface, each of said component spaces being a space surrounded by a surface, which cuts said interior spherical surface, and said frontier spherical surface, providing-probe points on said frontier surrounding surface of each of said component spaces at regular intervals;

deriving a rate of said molecule surrounding space occupied by each of said component spaces, as a space occupied rate of each of said component spaces;

deriving electrostatic energies between a unit charge set at each of said probe points and charges of all of atoms of said molecule, for each of said probe points on said frontier surrounding surface of each of said component spaces, and deriving the sum of said electrostatic energies on said frontier surrounding surface of a corresponding one of said component spaces, as an electrostatic factor of said corresponding one of said component spaces;

deriving van der Waals energies between a probe atom, which is set at each of said probe points and which has predetermined steric characteristic and all of said atoms of said molecule for each of said probe points on said frontier surrounding surface of each of said component spaces, and deriving the sum of said van der Waals energies on said frontier surrounding surface of said corresponding one of said component spaces, as a steric factor of said corresponding one of said component spaces;

assuming that said space occupied rate, said electrostatic factor and said steric factor are reaction characteristic values of said corresponding one of said component spaces, deriving the reaction characteristic values for all the component spaces of a predicting molecule of which a reaction characteristic is to be predicted, forming a predicting vector having a plurality of vector components selected from the reaction characteristic values of the predicting molecule, selecting a plurality of data molecules, a reaction characteristic of each of the data molecules being known, deriving the reaction characteristic values for all the component spaces of each of the data molecules, forming a data vector for each of the data molecules, the data vector being corresponding to the predicting vector and having a plurality of vector components selected from the reaction characteristic values of each of the data molecules, estimating a Euclid distance between the predicting vector and each data vector and getting a plurality of Euclid distances between the predicting vector and all the data molecules, and predicting the reaction characteristic of the predicting molecule to be that the reaction characteristic of the predicting molecule is more similar to a reaction characteristic of a data molecule related to a shorter Euclid distance.

15. A molecular reaction characteristic predicting method as set forth in claim 14, wherein said frontier surrounding surface is said frontier spherical surface.

16. A molecular reaction characteristic predicting method comprising the steps of:

describing atomic spherical surfaces, each of which surrounds a corresponding one of atoms of the molecule;

assuming that a portion of each of said atomic spherical surfaces intersecting the atomic spherical surfaces of other atoms of said molecule is an interior spherical surface;

assuming that a portion of each of said atomic spherical surfaces other than said interior spherical surface is a frontier spherical surface, the frontier spherical surface being appeared outside;

providing probe points on each of said atomic spherical surfaces at regular intervals;

deriving a rate of occupied space as a space occupied rate of a corresponding one of said atoms, for each of said atoms;

deriving electrostatic energies between a unit charge set at each of said probe points and charges of all of said atoms of said molecule, for each of said probe points on said frontier spherical surface of each of said atoms;

deriving the sum of said electrostatic energies on said frontier surrounding surface of a corresponding one of said atoms, as an electrostatic factor of said corresponding one of said atoms;

deriving van der Waals energies between a probe atom, which is set at each of said probe points and which has a predetermined steric characteristic, and all of said atoms of said molecule, for each of said probe points on said frontier surrounding surface of said atoms;

deriving the sum of said van der Waals energies on said frontier surrounding surface of said corresponding one of said atoms, as a steric factor of said corresponding on of said atoms;

assuming that said space occupied rate, said electrostatic factor and said steric factor are reaction characteristic values of said corresponding one of said atoms, deriving the reaction characteristic values for all the atoms of a predicting molecule of which a reaction characteristic is to be predicted, forming a predicting vector having a plurality of vector components selected from the reaction characteristic values of the predicting molecule, selecting a plurality of data molecules, a reaction characteristic of each of the data molecules being known, deriving the reaction characteristic values for all the component spaces of each of the data molecules, forming a data vector for each of the data molecules, the data vector being corresponding to the predicting vector and having a plurality of vector components selected from the reaction characteristic values of each of the data molecules, estimating a Euclid distance between the predicting vector and each data vector and getting a plurality of Euclid distances between the predicting vector and all the data molecules; and predicting the reaction characteristic of the predicting molecule to be that the reaction characteristic of the predicting molecule is more similar to a reaction characteristic of a data molecule related to a shorter Euclid distance.

17. A computer-readable storage medium having stored a program for predicting a reaction characteristic of a molecule, said program carrying out a process comprising the steps of:

setting a molecule surrounding surface surrounding the molecule so as to be reflected in a spatial dimension of a molecule, and assuming that a space surrounded by said molecule surrounding surface is a molecule surrounding space;

dividing said molecule surrounding space into a plurality of component spaces, by which a reaction characteristic of said molecule is characterized, in accordance with a predetermined space dividing procedure, and assuming that contour surfaces surrounding said component spaces are component surrounding surfaces, said molecule surrounding space being divided so as that each component space of the plurality of component spaces includes therein each one atom composing the molecule;

assuming that a portion of each of said component surrounding surfaces appearing outside on said molecule surrounding surface is a frontier surrounding surface of each of said component spaces;

providing probe points on said frontier surrounding surface of each of said component spaces at regular intervals;

deriving a rate of said molecule surrounding space occupied by each of said component spaces, as a space occupied rate of each of said component spaces;

deriving electrostatic energies between a unit charge set at each of said probe points and charges of all of atoms of said molecule, for each of said probe points on said frontier surrounding surface of each of said component spaces, and deriving the sum of said electrostatic energies on said frontier surrounding surface of a corresponding one of said component spaces;

deriving van der Waals energies between a probe atom, which is set at each of said probe points and which has a predetermined steric characteristic, and all of said atoms of said molecule, for each of said probe points on said frontier surrounding surface of each of said component spaces, and deriving the sum of said van der Waals energies on said frontier surrounding surface of said corresponding one of said component spaces as a steric factor of said corresponding one of said component spaces; and assuming that said space occupied rate, said electrostatic factor and said steric factor are reaction characteristic values of said corresponding one of said component spaces, deriving the reaction characteristic values for all the component spaces of a predicting molecule of which a reaction characteristic is to be predicted, forming a predicting vector having a plurality of vector components selected from the reaction characteristic values of the predicting molecule, selecting a plurality of data molecules, a reaction characteristic of each of the data molecules being known, deriving the reaction characteristic values for all the component spaces of each of the data molecules, forming a data vector for each of the data molecules, the data vector being corresponding to the predicting vector and having a plurality of vector components selected from the reaction characteristic values of each of the data molecules, estimating a Euclid distance between the predicting vector and each data vector and getting a plurality of Euclid distances between the predicting vector and all the data molecules, and predicting the reaction characteristic of the predicting molecule to be that the reaction characteristic of the predicting molecule is more similar to a reaction characteristic of a data molecule related to a shorter Euclid distance.

18. A molecular reaction characteristic predicting method for predicting n reaction characteristic of a molecule, said method consisting essentially of the steps of:

setting a molecule surrounding surface surrounding the molecule so as to be reflected in a spatial dimension of the molecule, and assuming that a space surrounded by said molecule surrounding surface is a molecule surrounding space;

dividing said molecule surrounding space into a plurality of component spaces, by which a reaction characteristic of said molecule is characterized, in accordance with a predetermined space dividing procedure, and assuming that contour surfaces surrounding said component spaces are component surrounding surfaces, said molecule surrounding space being divided so that each component space of the plurality of component spaces includes therein each one atom composing the molecule;

assuming that a portion of each of said component surrounding surfaces appearing outside on said molecule surrounding surface is a frontier surrounding surface of each of said component spaces;

providing probe points on said frontier surrounding surface of each of said component spaces at regular intervals;

deriving a rate of said molecule surrounding space occupied by each of said component spaces, as a space occupied rate of each of said component spaces;

deriving electrostatic energies between a unit charge set at each of said probe points and charges of all of atoms of said molecule, for each of said probe points on said frontier surrounding surface of each of said component spaces, and deriving the sum of said electrostatic energies on said frontier surrounding surface of a corresponding one of said component spaces, as an electrostatic factor of said corresponding one of said component spaces;

deriving van der Waals energies between a probe atom, which is set at each of said probe points and which has a predetermined steric characteristic, and all of said atoms of said molecule, for each of said probe points on said frontier surrounding surface of each of said component spaces, and deriving the sum of said van der Waals energies on said frontier surrounding surface of said corresponding one of said component spaces, as a steric factor of said corresponding one of said component spaces;

assuming that said space occupied rate, said electrostatic factor and said steric factor are reaction characteristic values of said corresponding one of said component spaces, deriving the reaction characteristic values for all the component spaces of a predicting molecule of which a reaction characteristic is to be predicted, forming a predicting vector having a plurality of vector components selected from the reaction characteristic values of the predicting molecule, selecting a plurality of data molecules; a reaction characteristic of each of the data molecule being known, deriving the reaction characteristic values for all the component spaces of each of the data molecules, forming a data vector for each of the data molecules, the data vector being corresponding to the predicting vector and having a plurality of vector components selected from the reaction characteristic values of each of the data molecules, estimating a Euclid distance between the predicting vector and each data vector and getting a plurality of Euclid distances between the predicting vector and all the data molecules, and predicting the reaction characteristic of the predicting molecule to be that the reaction characteristic of the predicting molecule is more similar to a reaction characteristic of a data molecule related to a shorter Euclid distance.

* * * * *